(12) United States Patent
Patchett et al.

(10) Patent No.: US 6,552,043 B1
(45) Date of Patent: Apr. 22, 2003

(54) BENZIMIDAZOLINYL PIPERIDINES AS CGRP LIGANDS

(75) Inventors: Arthur A. Patchett, Westfield, NJ (US); Raymond George Hill, Royston (GB); Lihu Yang, Edison, NJ (US)

(73) Assignees: Merck Sharpe & Dohme Ltd., Hertfordshire (GB); Merck & Co, Inc., Rahway, NJ (US)

( * ) Notice: Subject to any disclaimer, the term of this patent is extended or adjusted under 35 U.S.C. 154(b) by 0 days.

(21) Appl. No.: 09/806,372

(22) PCT Filed: Sep. 22, 1999

(86) PCT No.: PCT/GB99/03154

§ 371 (c)(1),
(2), (4) Date: May 30, 2001

(87) PCT Pub. No.: WO00/18764

PCT Pub. Date: Apr. 6, 2000

Related U.S. Application Data

(60) Provisional application No. 60/102,492, filed on Sep. 30, 1998.

(51) Int. Cl.⁷ ..................... A61K 31/445; C07D 609/14
(52) U.S. Cl. ................ 514/322; 514/321; 514/323; 546/199; 546/202; 546/205
(58) Field of Search ................ 514/321, 322, 514/323; 546/199, 202, 205

(56) References Cited

U.S. PATENT DOCUMENTS 5,442,044 A 8/1995 Hoover et al.
6,025,372 A * 2/2000 Yang et al. ............... 514/316
6,057,338 A * 5/2000 Yang et al. ............... 514/321
6,063,796 A * 5/2000 Yang et al. ............... 514/322

FOREIGN PATENT DOCUMENTS

| DE | 196 36 623 A1 | 3/1998 |
| WO | WO 98/11128 | 3/1998 |
| WO | WO 98/44921 | 10/1998 |
| WO | WO 98/44922 | 10/1998 |
| WO | WO 98/45285 | 10/1998 |

OTHER PUBLICATIONS

Netti et al. "Evidence of a central inhibition of growth hormone secretion by calcitonin gene–related peptide" CA 110:206266 (1989).*
Caignard "Structural activity relationships of jelatonin agonistic.antagonistis" CA 126:70291 (1994).*
Patani et al. "Bioisosterism; a rational approach in drug design" Chem. Rev. 96 3147–76 (1996) p. 3147.*
Allainmat et al. "Central and peripheral nervous systems . . . " Exp. Opin. ther. Patents, 7:1447–1458 (1997).*
Panani, et al.—Chem. Rev., vol. 96, p. 3147, 1996.
Allainmat, et al.—Exp. Opion. Ther. Pat., vol. 7, pp. 1447–1458, 1997.
Netti, et al.—CA 110:206266, 1989.
Caignard—CA 126:70291, 1994.

* cited by examiner

*Primary Examiner*—Ceila Chang
(74) *Attorney, Agent, or Firm*—Raynard Yuro; David L. Rose

(57) ABSTRACT

The present invention relates to benzimidazolinylpiperidine derivatives useful as ligands for CGRP (Calcitonin Gene-Related Peptide) receptors, their use in therapy, pharmaceutical compositions comprising them and methods of treatment using them.

5 Claims, No Drawings

BENZIMIDAZOLINYL PIPERIDINES AS CGRP LIGANDS

This application is a US National Phase application under 35 U.S.C. §371 of PCT Application No. PCT/GB99/03154, filed on Sep. 22, 1999, which claims priority under 35 U.S.C. 119 to U.S. Provisional No. 60/102,492, filed on Sep. 30, 1998.

The present invention relates to benzimidazolinylpiperidine derivatives useful as ligands for CGRP (Calcitonin Gene-Related Peptide) receptors, processes for their preparation, their use in therapy, pharmaceutical compositions comprising them and methods of treatment using them.

CGRP is a naturally occurring 37-amino acid peptide that is generated by tissue-specific alternate processing of calcitonin messenger RNA and is widely distributed in the central and peripheral nervous system. CGRP is localised predominantly in sensory afferent and central neurons and exhibits several biological actions, including vasodilation. CGRP is expressed in α- and β-forms that vary by one and three amino acids in the rat and human, respectively.

CGRPα and CGRPβ display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human (h) CGRP-(8–37)α, a fragment of CGRP that lacks seven N-terminal amino acid residues, is a selective antagonist of $CGRP_1$-Rs, whereas the linear analogue of CGRP, diacetoamido methyl cysteine CGRP ([Cys(ACM)2, 7]CGRP), is a selective agonist of $CGRP_2$-Rs.

We have now surprisingly found a class of compounds which are ligands, and preferably antagonists for CGRP receptors. In particular, they preferably bind selectively to human rather than rodent CGRP.

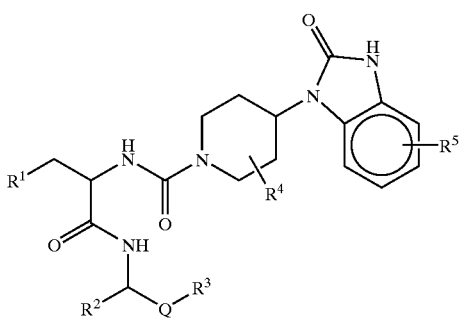

(I)

wherein:

$R^1$ is naphthyl or benzothienyl which is unsubstituted or substituted at up to three substitutable positions independently by $C_{1-6}$ alkyl, halogen, $C_{1-6}$ alkoxy, $CF_3$, $OCF_3$, $NO_2$, CN, methylenedioxy or ethylenedioxy;

$R^2$ is hydrogen, $C_{1-8}$ alkyl, —$(CH_2)_t$-aryl wherein aryl is selected from phenyl, biphenyl and naphthyl, —$(CH_2)_t$-heteroaryl wherin heteroaryl is selected from tetrazolyl, oxadiazolyl, thiadiazolyl, triazolyl and pyrazinyl, —$(CH_2)_qC(O)OR^6$, —$(CH_2)_qOR^6$, —$(CH_2)_qOC(O)R^6$, —$(CH_2)_qC(O)R^6$, —$(CH_2)_qC(O)(CH_2)_t$aryl, —$(CH_2)_qN(R^6)C(O)R^6$, —$(CH_2)_qC(O)N(R^6)_2$, —$(CH_2)_qN(R^6)SO_2R^6$, —$(CH_2)_qN(R_6)C(O)N(R^6)_2$, —$(CH_2)_qOC(O)N(R^6)_2$, —$(CH_2)_qN(R^6)C(O)OR^6$, —$(CH_2)_qN(R^6)SO_2N(R^6)_2$ and —$(CH_2)_qS(O)_{ml}R^6$;

$R^3$ is $NH_2$;

$R^4$ is hydrogen, $C_{1-6}$ alkyl, $C_{1-6}$ alkoxy, halogen, $OCF_3$ or $CF_3$;

$R^5$ is hydrogen, $C_{1-6}$ alkyl, $C_{1-6}$ alkoxy, halogen, $OCF_3$ or $CF_3$;

$R^6$ is hydrogen, $C_{1-8}$ alkyl or $C_{3-7}$ cycloalkyl, and when two $R^6$ groups are present and both represent $C_{1-8}$ alkyl they may optionally together with the atom to which they are both attached form a $C_{3-8}$ ring;

Q is —$(CH_2)_x$—$C(R^7)(R^{7a})$—$(CH_2)_y$— or —$(CH_2)_x$—V—$(CH_2)_y$—;

$R^7$ and $R^{7a}$ are independently chosen from hydrogen, $CF_3$, halogen, $C_{1-6}$ alkyl and $C_{1-6}$ alkoxy;

V is a $C_{3-8}$ non-aromatic cyclic or bicyclic ring or an aromatic ring which is benzene or naphthalene, said ring being unsubstituted or substituted at up to three substitutable positions independently by $C_{1-6}$ alkyl, $C_{1-6}$ alkoxy, halogen, $OCF_3$, $CF_3$, CN, $NO_2$, methylenedioxy or ethylenedioxy;

m is 0, 1 or 2;

q is 0, 1, 2, 3 or 4;

t is 0, 1, 2 or 3;

x and y are independently 0, 1, 2, 3 or 4;

or a pharmaceutically acceptable salt thereof.

$R^1$ is preferably unsubstituted or substituted with one or two groups selected from methyl, methoxy, $CF_3$ or halogen. Most preferably $R^1$ is unsubstituted.

$R^2$ is preferably hydrogen, methyl or $(CH_2)_qC(O)OR^6$, for example $R^2$ is 'butyloxycarbonyl or hydrogen.

$R^4$ is preferably hydrogen, methyl, methoxy, halogen, $OCF_3$ or $CF_3$. In particular, $R^4$ is hydrogen.

$R^5$ is preferably hydrogen, methyl, methoxy, halogen $OCF_3$ or $CF_3$. In particular $R^5$ is hydrogen.

$R^6$ is preferably hydrogen, $C_{1-4}$ alkyl or $C_{5-6}$ cycloalkyl. In particular $R^6$ may be hydrogen or 'butyl.

$R^7$ and $R^{7a}$ are preferably independently chosen from hydrogen, halogen, $CF_3$, methyl, methoxy and $OCF_3$. In particular both are hydrogen.

V is preferably an unsubstituted or substituted $C_{5-6}$ cycloalkyl or benzene. It is to be noted that the group $(CH_2)_y$ or, as the case may be $R^3$ is attached to any position of this ring, but the 3- and 4-positions are preferred. Most particularly V is cyclohexane or benzene.

m is preferably 0 or 2 q is preferably 0, 1 or 2 t is preferably 0 or 1 x+y is preferably 0, 1, 2, 3 or 4, in particular 0 or 3.

Thus there is a preferred subclass of compounds of formula Ia:

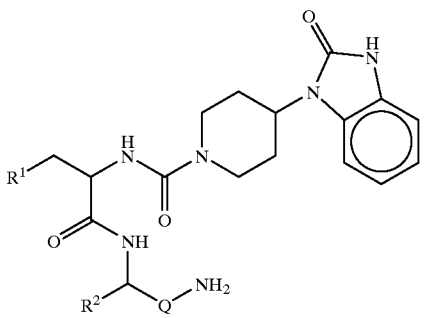

(I)

wherein $R^1$ is unsubstituted naphthyl or benzothienyl;
$R^2$ is hydrogen or $C(O)OR^6$;
$R^6$ is $C_{1-4}$ alkyl;
Q is —$(CH_2)_x$—$C(R^7)(R^{7a})$—$(CH_2)_y$— or —$(CH_2)_x$—V—$(CH_2)_y$—;
V is cycloalkyl or benzene;
x is 0, 1 or 2;
y is 0, 1 or 2;
or a pharmaceutically acceptable salt thereof.

The term "alkyl" refers to a monovalent alkane (hydrocarbon) derived radical which may be straight, branched or cyclic. Examples of alkyl groups are methyl, ethyl, propyl, isopropyl, butyl and t-butyl. "Alkoxy" groups are to be construed analogously.

The term "$C_{3-8}$ cyclic ring" includes groups such as cyclopentyl, cyclohexyl and methylcyclohexyl.

The term "halogen" is intended to include fluorine, chlorine, bromine and iodine.

Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate. A preferred salt is Hydrochloride.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

A preferred chiral configuration of the compounds of formula I is:

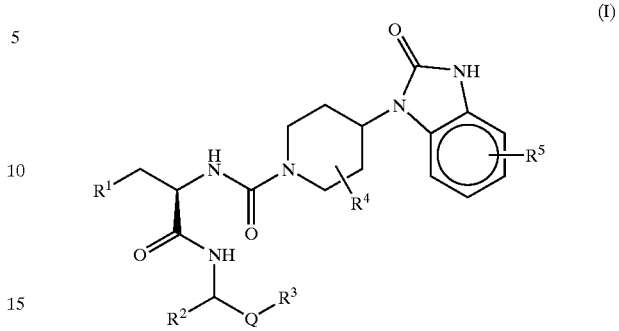

(I)

The ability of the compounds of the present invention to act as ligands for CGRP makes them useful as pharmacological agents for humans and animals, but particularly humans, for the treatment and prevention of disorders where CGRP may be involved. Such disorders include migraine, pain, cardiovascular disorders, inflammation, diabetes, Reynaud's syndrome, peripheral arterial insufficiency, subarachnoid and other cranial haemorrhages and as antitumour agents by controlling the flow of blood to tumours. Of these conditions, the treatment of migraine is particularly important.

The present invention therefore also provides a pharmaceutical composition comprising a compound of the present invention or a pharmaceutically acceptable salt thereof and a pharmaceutically acceptable excipient.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The present invention also provides a compound of the present invention or a pharmaceutically acceptable salt thereof for use in a method of treatment of the human or animal body by surgery, therapy or diagnosis.

There is also provided the use of a compound of the present invention or a pharmaceutically acceptable salt thereof for the manufacture of a medicament for the treatment of a condition with which CGRP is associated such as migraine, pain, cardiovascular disorders, inflammation, diabetes, Reynaud's syndrome, peripheral arterial insufficiency, subarachnoid and other cranial haemorrhages and tumours by controlling blood flow.

There is further disclosed a method of treating or protecting a subject suffering from or prone to a condition associated with CGRP by administering to that subject a therapeutically or prophylactically effective amount of a compound of the present invention or a pharmaceutically acceptable salt thereof.

The preparation of compounds of Formula I of the present invention may be carried out in sequential or convergent synthetic routes. Syntheses detailing the preparation of the compounds of Formula I are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMIF or mixtures thereof, followed by addition of the second amine and a base such as NMM, TEA or DIEA. The uses of protective groups for amines and carboxylic acids to facilitate the desired reaction and minimize undesired reactions are well documented.

Conditions required to remove protecting groups which may be present can be found in Greene, T, and Wuts, P. G. M., *Protective Groups in Orgaitic Synthesis*, John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula 1 are, in many cases, commercially available, where the protecting group ($P^1$) is, for example, methyl, allyl or benzyl groups. Other protected amino acid can be prepared by literature methods (Williams, R. M. *Synthesis of Optically Active α-Amino Acids*, Pergamon Press: Oxford, 1989). Many of the piperidines of Formula 2 are either commercially available or known in the literature and others can be prepared following literature methods described for analogous compounds. Some of these methods are illustrated in the subsequent schemes. Purification procedures include crystallization, normal phase or reverse phase chromatography.

The compounds of the present invention can be prepared readily according to the following Schemes or modifications thereof using readily available starting materials, reagents and conventional synthesis procedures. In these reactions, it is also possible to make use of variants which are themselves known to those of ordinary skill in this art, but are not mentioned in greater detail. The definition for $R^1$, $R^2$, $R^3$, $R^4$, $R^5$, $R^6$, $R^7$, $R^{7a}$ and Q is described above unless otherwise stated.

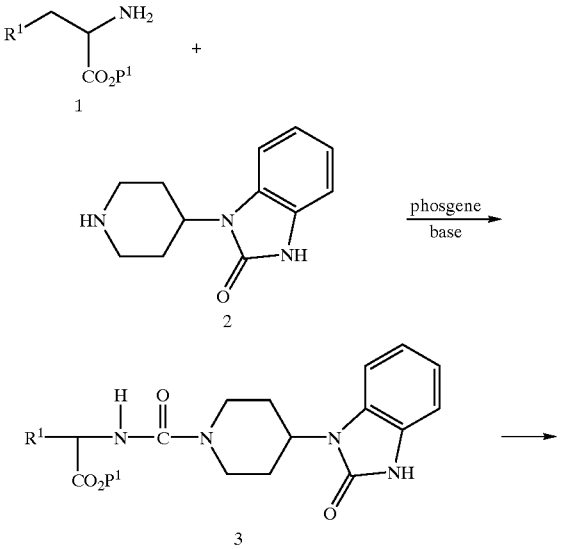

SCHEME 1

-continued

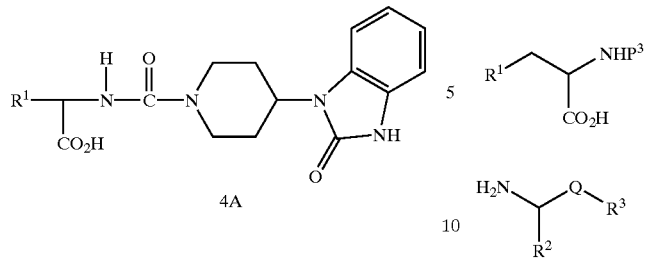

4A

Intermediates of Formula 4A can be synthesized as described in Scheme 1. Mixed urea formation between the protected amino acid 1 and the piperidine of Formula 2, is conveniently carried out under usual urea formation reactions use phosgene or equivalents such as CDI, DSC, or p-nitrophenyl chloroformate. Removal of the $P^1$ protecting group can be achieved by saponification for most esters, or by catalytic hydrogenolysis when $P^1$ is benzyl, or by palladium (0) based homogeneous catalysis when $P^1$ is allyl. Intermediate 4A can be used as a common intermediate with variation of the rest of the molecule of Formula I as shown in Scheme 2.

SCHEME 2

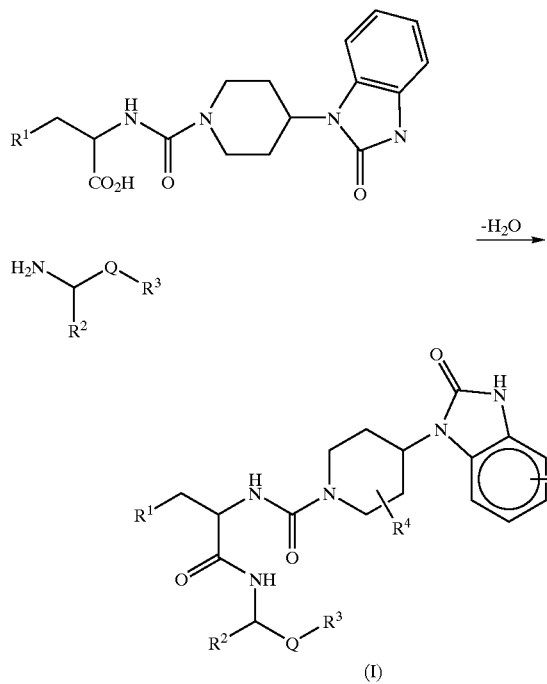

(I)

Intermediates of formula 4 (the first compound above) can be coupled to intermediates of formula 5 (the second compound above) under standard ester or peptide coupling reaction conditions. Primary amine $R^3$ may be protected by a group such as BOC, Cbz, etc. which is subsequently removed. Many of the selectively protected diamines or amino alcohols of Formula 5 are either commercially available or known in the literature and others can be prepared following literature methods described for analogous compounds. Some of these methods are illustrated in subsequent schemes. The compound 4 is also generally protected with a protecting group as defined above.

SCHEME 3

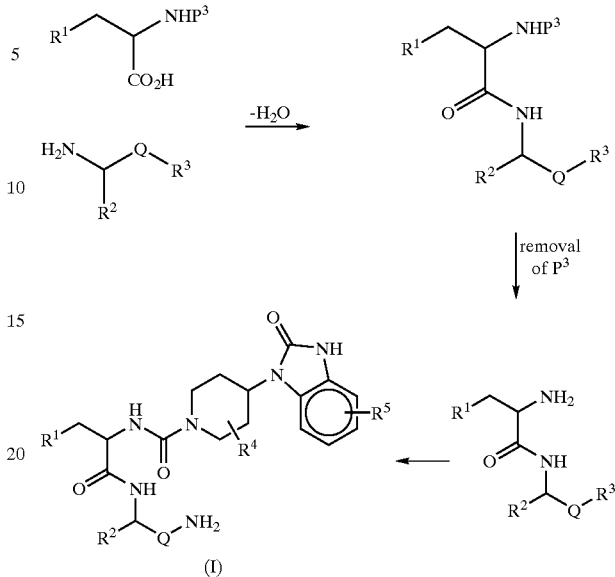

(I)

Alternatively, compounds of Formula I can be prepared starting from compound 5. The protected amino acid derivatives 8 (the first compound above) are in many cases commercially available, where P3 is, for example, BOC, Cbz, Fmoc, and the like. N-Protected amino acid 8 can be coupled to intermediates of formula 5, to afford compounds of Formula 9 (the first product above) under standard ester or peptide coupling reaction conditions. The protecting group in compound 8 is selected with the criteria that its removal can be achieved without removing $P^2$. When the $P^2$ protecting group is removed to afford compound 10 (the second product above), this compound can be further converted to compounds of formula I-A according to the procedures described in Scheme 1. Again $R^3$ is optionally protected.

SCHEME 4

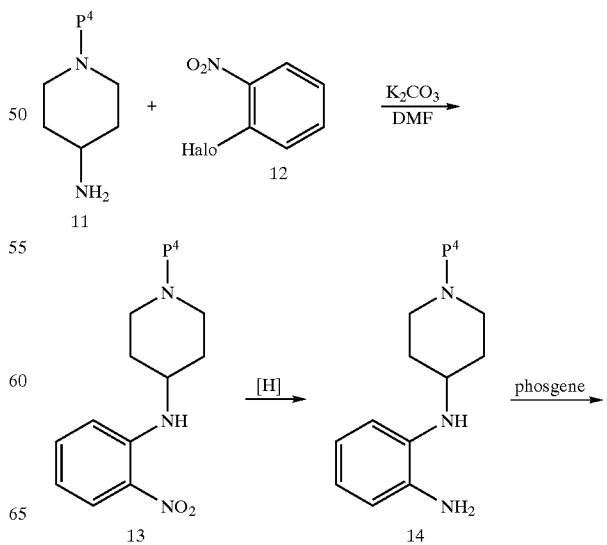

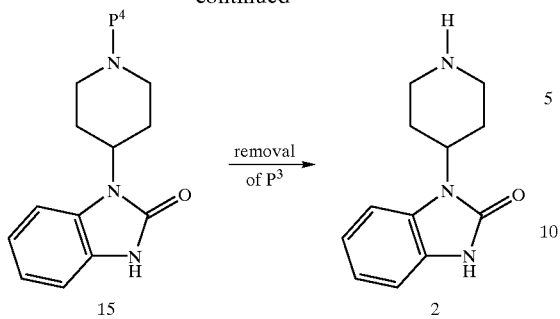 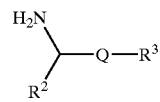

The piperidinylbenzimidazolinone 2 without substitution is commercially available; derivatives with substituents on the benzene ring are prepared by the methods shown in Scheme 4 as described in *J. Med. Chem.*, 30, 814–819 (1987) and U.S. Pat. No. 3,910,930, hereby incorporated by reference. $P^4$ is a protecting group such as benzyl, methyl, BOC, Cbz, ethyloxycarbonyl and the like. Thus, condensation of the commercially available 4-aminopiperidine 11, where $P^4$ is C(O)OEt, with a substituted o-halo nitrobenzene 12 gives the nitro compound 13. Reduction of the nitro group to an amine can be accomplished by catalytic hydrogenation with a catalyst such as Raney Ni, palladium on carbon or platinum on carbon in a protic solvent such as ethanol. Ring closure can be effected by phosgene or its equivalent such as DSC, CDI in the presence of a base. The protecting group $P^4$ can be removed by alkaline hydrolysis in the case of C(O)OEt or can be removed by the standard deprotection conditions as described in Greene, T, and Wuts, P. G. M., *Protective Groups in Organic Synthesis*, John Wiley & Sons, Inc., New York, N.Y. 1991.

In many cases, compounds of Formula 5 or its mono protected form within the scope of this invention are either commercially available or known in the art. Mono Boc protected amine can be prepared by reacting excess diamine with $Boc_2O$ in methanol, where Boc protected amino alcohols can be preprared by reacting the amino alcohol with $BOc_2O$.

Other compounds in the above schemes are commercially available or can be made from commercially available compounds by standard methods.

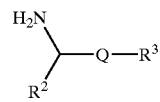

Compounds of Formula 5 can be amino acids, which in some cases are commercially available. Amino acids can be modified to give compounds as defined by the scope of the instant application. For example, with the two amino groups properly protected, the carboxylic acid can be converted into its next higher homologue, or to a derivative of the homologous acid, such as amide or ester by an Arndt-Eistert reaction. The acid can also be converted amides with a variety of amines as defined. The acid can be reduced to alcohol, which can be converted to ether by alkylation or reduced with methods known to those skilled in the art.

Optically pure cis-3-aminomethyl-1-BOC-aminomethyl cyclohexane enantiomers are prepared (Scheme 5) starting from commercially available m-cyanobenzoic acid. Reduction of the nitrile with Raney $Ni/H_2$ is followed by protection of the resulting 1° amino group. Reduction of the aromatic ring is then accomplished using $PtO_2$ as catalyst to give predominantly the cis-cyclohexane carboxylic acid. A sequence of crystallizations using either (S) or (R)-a-methylbenzylamine to form the salt, generates the homochiral cis acids as shown below. Enantiomeric purity is evaluated by derivatization of the acids with Trp-OMe and integration of the methoxy methyl singlets in the $^1H$ NMR spectra. The absolute stereochemistries are determined by solving the x-ray structure for the pure salt obtained from crystallization with the S-enantiomer of a-methylbenzylamine and are as shown in Scheme 5 below. Borane reduction of the pure acids, followed by coversion of the resulting alcohols to their mesylates and displacement with azide anion furnishes the corresponding azidomethyl compounds. Reduction of the azide group ($Pd/C$, $H_2$) gives the desired amines, ready for incorporation into final target compounds.

SCHEME 5

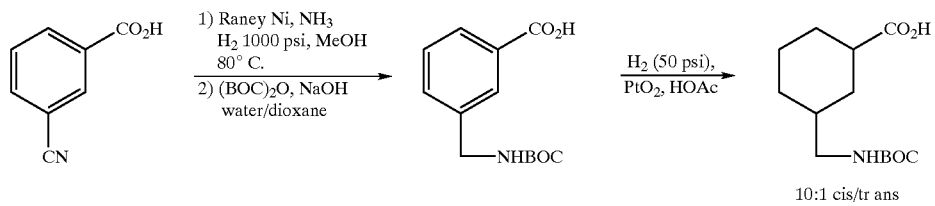

10:1 cis/trans

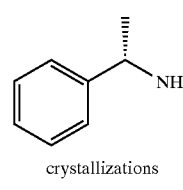

crystallizations

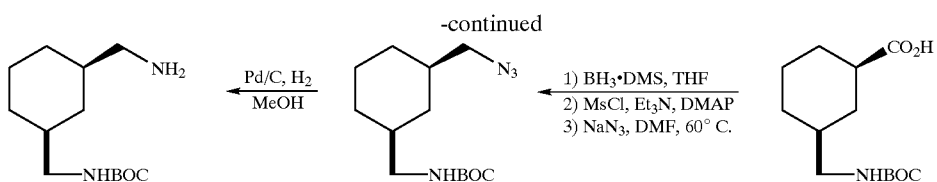

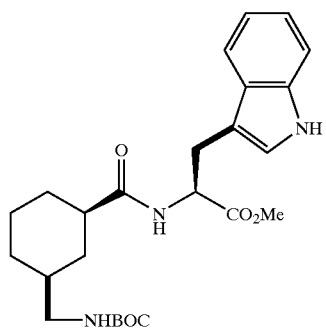

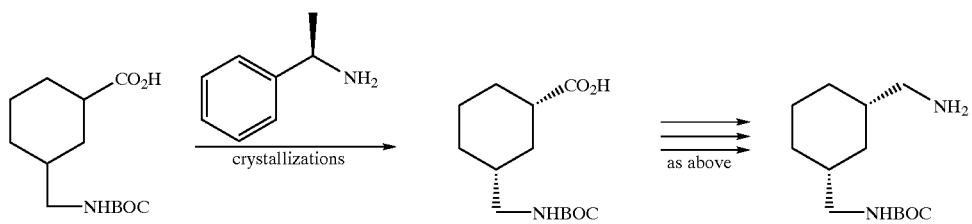

The racemic cis and trans-3-aminomethyl-1-BOC-aminomethyl cyclohexane isomers are also prepared (Scheme 6) and incorporated into target compounds. Commercially available bis-aminomethylcyclohexane (sold as a mixture of cis and trans isomers) is resolved into the pure cis and pure trans isomers by conversion to the dihydrochloride salts and crystallization from methanol/ethyl acetate. Mono-BOC protection is accomplished by slow addition of $BOC_2O$ to an excess of the diamines.

SCHEME 6

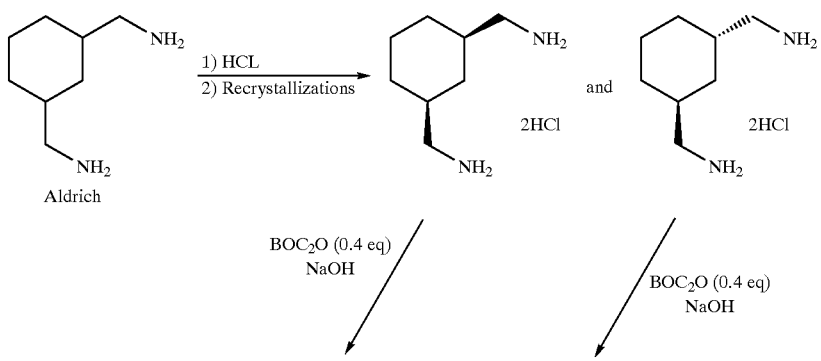

-continued

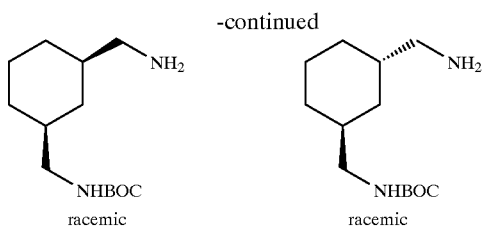
racemic    racemic

Trans-1-N-BOC-amino-4-aminomethylcyclohexanes are prepared from the commercially available amino acid shown below (Scheme 10). Protection of the amine as its phthalimide, followed by Curtius rearrangement gives the amino-protected isocyanate. Trapping of the isocyanate with t-butanol, is then followed by removal of the phthalimide protecting group using hydrazine to provide the target amine, which is incorporated into various analogs.

SCHEME 10

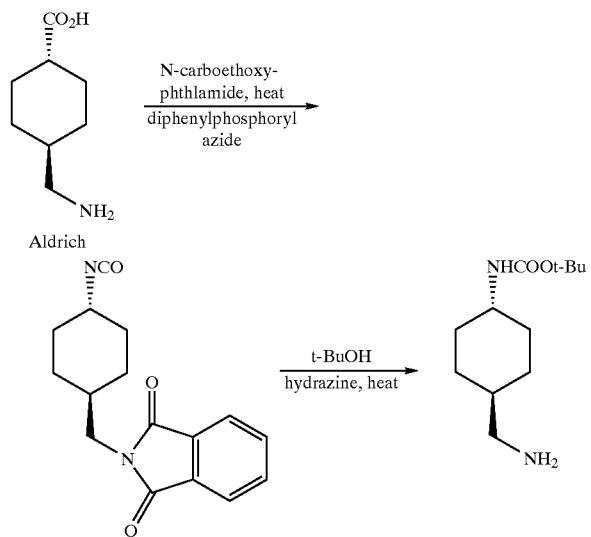

Mono-protected-1,3-bisaminomethylbenzene intermediates also lead to potent analogs. These are prepared (Scheme 11) starting from commercially available in-xylylenediamine. Slow addition of $BOC_2O$ to an excess of diamine furnishes the mono-protected amine, which is employed in the synthesis of target compounds.

SCHEME 11

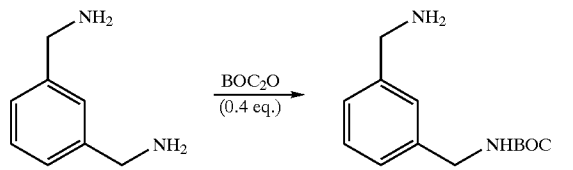

Racemic cis-3-aminomethyl-1-BOC-aminomethylcyclopentane is prepared as shown in Scheme 12. Reduction of the commercially available anhydride give cis-hydroxymethylcyclopentane. Conversion to the bis-mesylate, followed by displacement with azide results in the corresponding bis-azide. Reduction of the azide groups and mono-protection (as described previously) provides the desired intermediate amine.

SCHEME 12

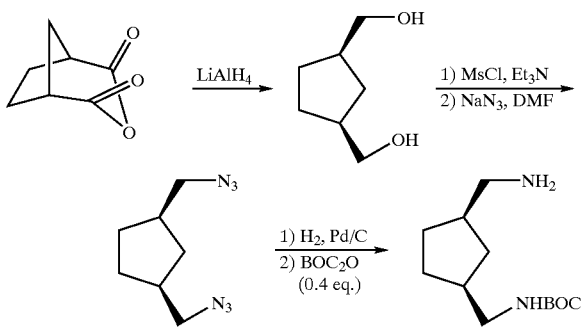

The compounds of the present invention have been tested in a cell assay for activity as ligands for the human CGRP receptor. The methodology for this is as described in Semark et al. Molecular Neuropharmacology (1992) 2, 311–317. Likewise their functional activity can be determined by methods in that paper. The specific Examples of the present invention all inhibited $[^{125}I]hCGRP$ in SK-N-MC cell membranes with a Ki of less than 10 $\mu M$.

The preferred compounds of the invention are any or all of those specifically set forth in the Examples below. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Intermediate 1

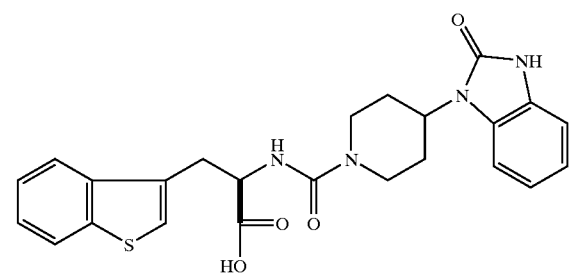

A suspension of D-β-(3-benzothienyl)alanine methyl ester (2.45 mmol), disuccinimidyl carbonate (0.626 g, 1.0 equiv.) and DIEA (0.426 mL, 4 equiv.) in dichloromethane (20 mL) was stirred at room temperature for 30 minutes, during which time the reaction becomes clear. 4-(2-Keto-1-benzimidazolinyl)piperidine (0.568 g) was added and the mixture was permitted to stir overnight. The reaction mixture was diluted with dichloromethane, and washed in succession with 1N HCl, saturated NaHCO₃ solution and brine, dried over MgSO₄, filtered and concentrated. The resulting crude product was purified by silica flash column chromatography eluting with ethyl acetate to afford the methyl ester intermediate (1.09 g).

To a stirred solution of the methyl ester (1.09 g) from the previous step in THF/AMeOH/H₂O (1:1:1) was added lithium hydroxide (384 mg) at 0° C. The reaction mixture was stirred for 4 h and was quenched by the addition of hydrochloric acid (2 equiv.). The mixture was then evaporated to remove the solvents, and partitioned between dilute hydrochloric acid and ethyl acetate. The organic extracts were washed with brine, dried over magnesium sulfate and evaporated to give the desired intermediate (1.1 g, crude).

Intermediate 2

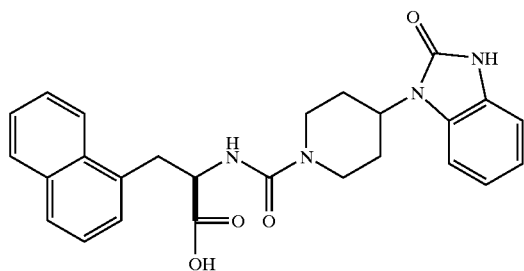

Intermediate 2 was similarly prepared as Intermediate 1 using D-β-(1-naphthyl)-Alanine methyl ester and 4-(2-Keto-1-benzimidazolinyl)piperidine.

EXAMPLE 1

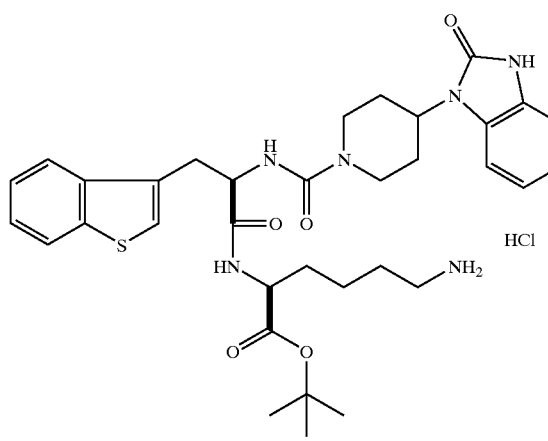

To a solution of Intermediate 1 (53 mg), HOBt (1 equiv.), and Lys(Cbz)OBu' (41 mg) in dichloromethane (2 mL) at 0° C., was added EDC (32 mg, 1.5 equiv.) and the resulting solution was stirred for 4 h. The reaction mixture was then diluted with dichloromethane and washed with dilute HCl, brine, saturated NaHCO₃ and dried over MgSO₄. After filtration and evaporation, the residue was purified by silica eluting with 2% methanol in ethyl acetate to give the Cbz intermediate (79 mg).

The intermediate prepared as described above (60 mg) was combined with 10% Pd/C (10 mg) and concentrated HCl (1 equiv.) inethanol (5 mL). This mixture was stirred under a H₂ balloon for 1 day and during which time 3 batches 10% Pd/C (10 mg each) was added. The mixture filtered through celite. The filter cake was washed with an additional 10 mL of ethanol and the combined filtrates were concentrated to give the desired product as a hydrochloride salt (50 mg).

EXAMPLE 2

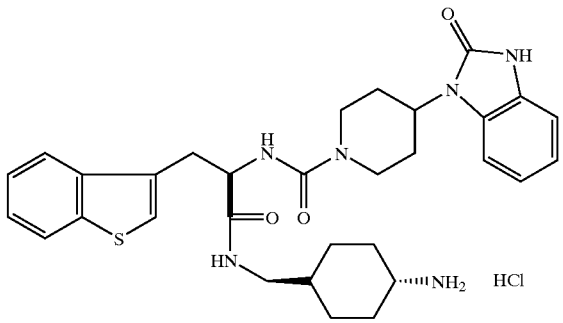

To a solution of Intermediate 1 (53 mg), HOBt (1 equiv.), and trans-4-aminomethyl-1-(cyclohexylmethyll-carbamic acid tert-butyl ester (58 mg) in dichloromethane (2 mL) at 0° C., was added EDC (32 mg, 1.5 equiv.) and the resulting solution was stirred for 4 h. The reaction mixture was then diluted with dichioromethane and washed with dilute HCl, brine, saturated NaHCO₃ and dried over MgSO₄. After filtration and evaporation, the residue was purified by silica eluting with 5% methanol in ethyl acetate to give the Boc intermediate (58 mg). Treatment of the intermediate with 4 N HCl in dioxane (1 mL) in ethyl acetate (2 mL) gave the desired product (41 mg) after evaporation.

EXAMPLE 3

To a solution of Intermediate 2 (120 mg), HOBt (1 equiv.), and 3-aminomethylbenzyl-carbamic acid tert-butyl ester (62 mg) in dichloromethane (5 mL) at 0° C., was added EDC (60 mg, 1.5 equiv.) and the resulting solution was stirred for 2 days during which time the reaction mixture was warmed to ambient temperature. The reaction mixture was diluted with dichloromethane and washed with dilute HCl, brine, saturated NaHCO₃ and dried over MgSO₄. After filtration and evaporation, the residue was purified by silica eluting with 7% methanol in ethyl acetate to give the Boc intermediate (110 mg). Treatment of the intermediate with 4 N HCl in dioxane (2 mL) in ethyl acetate (2 mL) gave the desired product (90 mg) after evaporation.

EXAMPLE 4

To a solution of Intermediate 2 (100 mg, 0.218 mmol), HOBt (31 mg, 1.05 equiv.), and [3(R)-aminomethyl-1(S)-cyclohexylmethyl]-carbamic acid tert-butyl ester (56 mg, 1.05 equiv.) in dichloromethane (8 mL) at 0° C., was added EDC (50 mg, 1.2 equiv.) and the resulting solution was stirred for 2 days. The reaction mixture was then diluted with dichloromethane and washed with dilute HCl, brine, saturated $NaHCO_3$ and dried over $MgSO_4$. After filtration and evaporation, the residue was purified by silica eluting with 7% methanol in ethyl acetate to give the Boc intermediate (100 mg). Treatment of the intermediate with 4 N HCl in dioxane (1 mL) in ethyl acetate (2 mL) gave the desired product after evaporation.

What is claimed is:

1. A compound of formula I (I)

wherein:

$R^1$ is naphthyl or benzothienyl which is unsubstituted or substituted at up to three substitutable positions independently by $C_{1-6}$ alkyl, halogen, $C_{1-6}$ alkoxy, $CF_3$, $OCF_3$, $NO_2$, CN, methylenedioxy or ethylenedioxy;

$R^2$ is hydrogen, $C_{1-8}$ alkyl, $-(CH_2)_t$-aryl wherein aryl is selected from phenyl, biphenyl and naphthyl, $-(CH_2)_t$-heteroaryl wherin heteroaryl is selected from tetrazolyl, oxadiazolyl, thiadiazolyl, triazolyl and pyrazinyl, $-(CH_2)_qC(O)OR^6$, $-(CH_2)_qOR^6$, $-(CH_2)_qOC(O)R^6$, $-(CH_2)_qC(O)R^6$, $-(CH_2)_qC(O)(CH_2)_t$aryl, $-(CH_2)_qN(R^6)C(O)R^6$, $-(CH_2)_qC(O)N(R^6)_2$, $-(CH_2)_qN(R^6)SO_2R^6$, $-(CH_2)_qN(R^6)C(O)N(R^6)_2$, $-(CH_2)_qOC(O)N(R^6)_2$, $-(CH_2)_qN(R^6)C(O)OR^6$, $-(CH_2)_qN(R^6)SO_2N(R^6)_2$ and $-(CH_2)_qS(O)_mR^6$;

$R^3$ is $NH_2$;

$R^4$ is hydrogen, $C_{1-6}$ alkyl, $C_{1-6}$ alkoxy, halogen, $OCF_3$ or $CF_3$;

$R^5$ is hydrogen, $C_{1-6}$ alkyl, $C_{1-6}$ alkoxy, halogen, $OCF_3$ or $CF_3$;

$R^6$ is hydrogen, $C_{1-8}$ alkyl or $C_{3-7}$ cycloalkyl, and when two $R^6$ groups are present and both represent $C_{1-8}$ alkyl they may optionally together with the atom to which they are both attached form a $C_{3-8}$ ring;

Q is $-(CH_2)_x-C(R^7)(R^{7a})-(CH_2)_y-$ or $-(CH_2)_x-V-(CH_2)_y-$;

$R^7$ and $R^{7a}$ are independently chosen from hydrogen, $CF_3$, halogen, $C_{1-6}$ alkyl and $C_{1-6}$ alkoxy;

V is a $C_{3-8}$ non-aromatic cyclic or bicyclic ring or an aromatic ring which is benzene or naphthalene, said ring being unsubstituted or substituted at up to three substitutable positions independently by $C_{1-6}$ alkyl, $C_{1-6}$ alkoxy, halogen, $OCF_3$, $CF_3$, CN, $NO_2$, methylenedioxy or ethylenedioxy;

m is 0, 1 or 2;

q is 0, 1, 2, 3 or 4;

t is 0, 1, 2 or 3;

x and y are independently 0, 1, 2, 3 or 4;

or a pharmaceutically acceptable salt thereof.

2. A compound of formula Ia:

(I)

wherein $R^1$ is unsubstituted naphthyl or benzothienyl;

$R^2$ is hydrogen or $C(O)OR^6$;

$R^6$ is $C_{1-4}$ alkyl;

Q is $-(CH_2)_x-C(R^7)(R^{7a})-(CH_2)_y-$ or $-(CH_2)_x-V-(CH_2)_y-$;

V is cycloalkyl or benzene;

X is 0, 1 or 2;

y is 0, 1 or 2;

or a pharmaceutically acceptable salt thereof.

3. A compound which is:

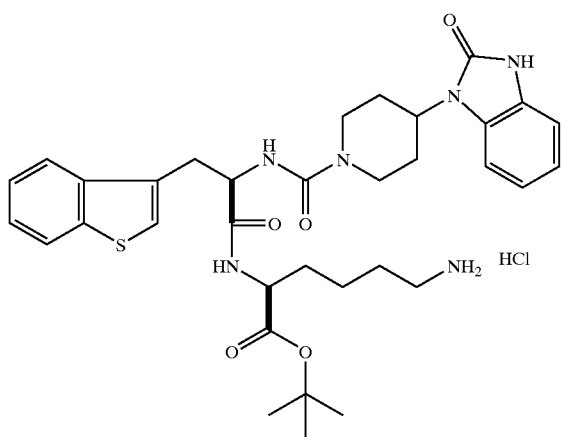

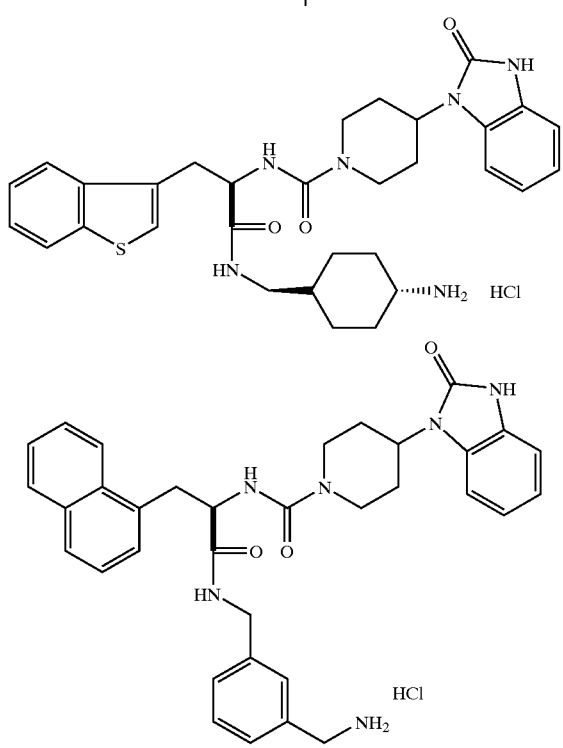

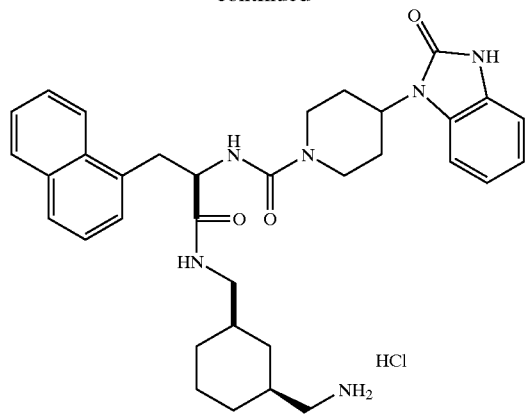

in free base form or as a pharmaceutically acceptable salt.

4. A pharmaceutical composition comprising a therapeutically effective amount of a compound of claim 1 or a pharmaceutically acceptable salt thereof and a pharmaceutically acceptable carrier.

5. A method of treating a disease or condition selected from the group consisting of:

(a) migraine,
(b) pain,
(c) cardiovascular disorder,
(d) inflammation,
(e) diabetes,
(f) Reynaud's syndrome,
(g) peripheral arterial insufficiency,
(h) cranial hemorrhage and
(i) tumor, comprising administering to said patient a therapeutically effective amount of a compound of claim 1 or a pharmaceutically acceptable salt thereof.

* * * * *